(12) United States Patent
Ullman et al.

(10) Patent No.: US 6,379,899 B1
(45) Date of Patent: Apr. 30, 2002

(54) ISOTHERMAL EXPONENTIAL RNA AMPLIFICATION IN COMPLEX MIXTURES

(75) Inventors: Edwin Ullman, Atherton; Ming Wu, Castro Valley, both of CA (US)

(73) Assignee: Discoverx, Fremont, CA (US)

( * ) Notice: Subject to any disclaimer, the term of this patent is extended or adjusted under 35 U.S.C. 154(b) by 0 days.

(21) Appl. No.: 09/805,674

(22) Filed: Mar. 13, 2001

(51) Int. Cl.$^7$ .............................. C12Q 1/68; C12P 19/34
(52) U.S. Cl. ........................................... 435/6; 435/91.2
(58) Field of Search ..................................... 435/6, 91.2

(56) References Cited

U.S. PATENT DOCUMENTS 6,025,133 A * 2/2000 Stull et al. ..................... 435/6

* cited by examiner

Primary Examiner—Eggerton A. Campbell
(74) Attorney, Agent, or Firm—Hana Verny

(57) ABSTRACT

Methods and compositions are provided for performing isothermal amplification of a nucleic acid target employing probes characterized by having a masked RNA polymer promoter unable to bind to a complementary initiator oligonucleotide and RNA polymerase and initiate transcription, a dsDNA sequence which when invaded by the target nucleic acid exposes the masked promoter to initiate transcription, and a template sequence, a portion of which is normally included in the dsDNA region, which when copied produces a product that can reinitiate the process of invading the dsDNA region and initiating transcription of another copy.

20 Claims, 1 Drawing Sheet

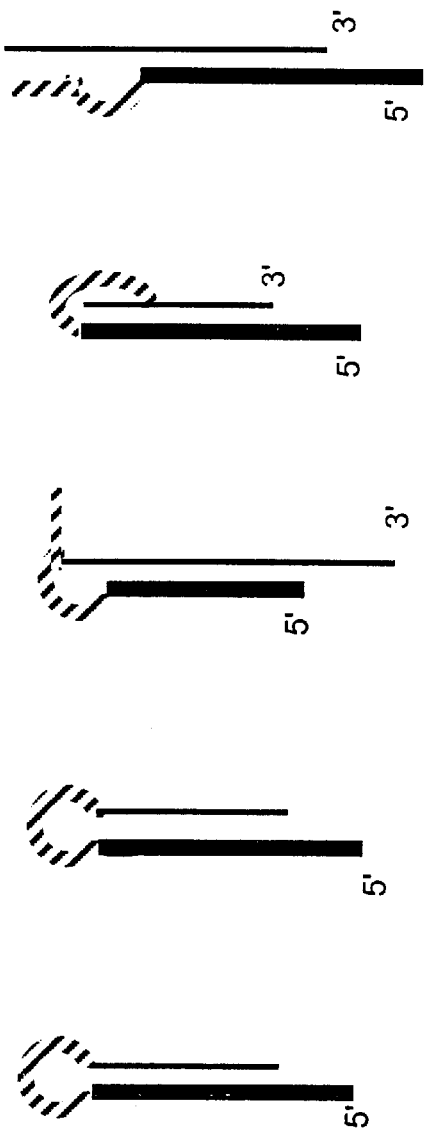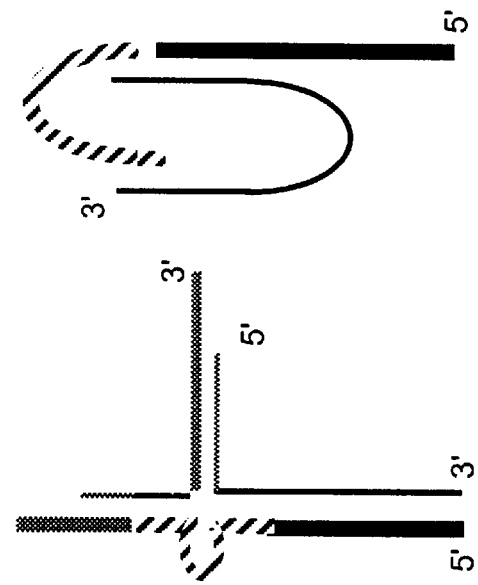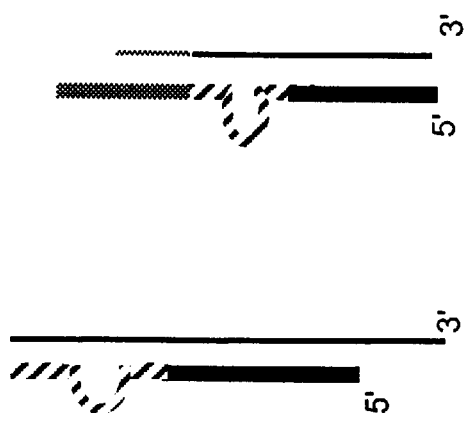

ISOTHERMAL EXPONENTIAL RNA AMPLIFICATION IN COMPLEX MIXTURES

TECHNICAL FIELD

The field of this invention is methods for determining ribonucleic acid.

BACKGROUND

There is substantial interest in being able to determine the occurrence and level of transcription in cells in vivo and in vitro. The transcriptional level is related to the strength of the promoter, the presence and amount of transcriptional factors, the level of binding of the transcriptional factors to the regulatory region, including the promoter and any enhancer, and the response of the cell to changes in its environment. Information concerning the occurrence of transcription and the level of mRNA produced can be associated with the pathways involved with the status of the cell, such as the type of cell, differentiation, maturation, response to internal and external changes, and the like. The information can be relevant to the effect of candidate drugs on the cell, the nature of the cell, as in metastatic cancer, active pathways in the cell, and other information of physiologic interest.

The amount of mRNA produced varies widely with the gene and the status of the cell. Frequently, the mRNA from the gene(s) of interest can be in very small amount, which can be further reduced by degradation by RNases, even when one quickly inactivates the RNases. In addition, since a single mRNA can be used as a template for the production of multiple copies of the encoded protein, very small amounts of mRNA may have profound effects on the physiology of the cell. In addition, one usually wishes to identify a small number of the total number of mRNAs that are present in the cell. In any system of amplification, there is always the concern that an mRNA that may be similar to the target(s) of interest may be present in much larger amount and becomes amplified. In this situation one will obtain a false negative, as the more abundant mRNA may obscure the detection of the less abundant mRNA. Methods of amplification should provide for high fidelity, so as minimize the opportunities for cross-reactivity with mRNAs other than the target mRNA(s).

There is also the fact that mRNAs have substantial secondary and tertiary structure. Unwinding the secondary and tertiary structure requires energy, so that the mRNA of interest may be less available to various methods of amplification, particularly isothermal amplification.

Numerous methods are found in the literature for detecting and amplifying mRNA, either as mRNA or cDNA. In many cases the methods require denaturation, so that one must use thermal cycling, which is inefficient. Where cDNA is used and the polymerase chain reaction is employed for amplification, not only is one concerned with thermal cycling, but the steps of reverse transcribing and amplification can introduce errors and the system is not useful for multiplexing. Other methods have used the $Q_\beta$ replicase, but the replicase is promiscuous and can and does produce copies of other than the target mRNA(s).

There is a need for methods that allow for multiplexing, so as to be able to amplify multiple mRNAs simultaneously without significant amplification of mRNAs other than the target mRNAs. Also, the method should permit high fidelity in copying the target mRNA and excluding other mRNAs. Desirably, the method should avoid thermal cycling and have a limited number of steps for amplification and identification of the target mRNAs and allow for a reasonable degree of quantitation. Other benefits would include a minimal number of reagents, stable reagents, exponential amplification, and ease of detection of the amplified product.

PRIOR ART

U.S. Pat. Nos. of interest include U.S. Pat. Nos. 4,725,537; 4,766,062; 4,795,701; 4,795,701; 4,957,858; 5,169,766; 5,385,834; 5,503,979; 5,620,851; 5,631,129; 5,916,779; 5,925,517; 6,037,130; 6,093,542; 6,100,024; 6,013,442; 6,132,997 and 6,180,338. Tm Bioscience Corp. (Toronto, Canada) sells hairpin capture probes as described in their brochures and on their web page. The T7 RNA polymerase is described in Sastry and Ross., Biochemistry (1997) 36:3133–44; Noren and Moreira, Book of Abstracts, $211_{th}$ ACS National Meeting, New Orleans, La., Mar. 24–28 (1996); Cheetham, et al., Nature (London) (1999) 399:80–83; and Maslak, et al., Biochemistry (1993) 32:4270–4. Other references of interest include Lohse, et al., Proc. Natl. Acad. Sci. USA (1999) 96:11804–8; Phillips and Eberwine, Methods (1996) 10:283–8; Breaker, et al., Biochemistry (1994) 33:11980–6; and Milligan, et al., Nucleic Acids Res. (1987) 15:8783–98.

U.S. Pat. No. 6,025,133 describes hairpin probes as "promoter-sequestered" oligonucleosides to achieve "target-triggered" amplification, which disclosure is specifically incorporated by reference in this application in its entirety.

SUMMARY OF THE INVENTION

Nucleic acid sequences are isothermally exponentially amplified using an RNA polymerase, a probe, a promoter initiator and RTPs. The probe comprises a masked promoter, and a double stranded nucleic acid region with a protruding sequence for binding to the target sequence to be amplified. Upon binding of the target to the protruding sequence, the target invades the double stranded region allowing the promoter initiator to bind to the masked promoter to provide a holopromoter initiating template dependent synthesis of RNA. Particularly, bulky groups are provided in proximity to the promoter region to inhibit transcription in the absence of target or target copy binding, particularly when a hairpin probe is used. The resulting RNA product can in turn act as the target nucleic acid invading probes and initiating additional copies of the target RNA.

BRIEF DESCRIPTION OF THE FIGURES

FIG. 1, A–J are diagrammatic views of probes according to this invention.

DESCRIPTION OF THE SPECIFIC EMBODIMENTS

Methods and compositions are provided for amplifying ribonucleic acids using a probe to which the target ribonucleic acid binds. The method is based on having a probe that comprises a masked promoter (single stranded promoter region, ssNA) that is substantially inactive in a first conformation of the probe and active in a second conformation of the probe, a double stranded nucleic acid region (dsNA), particularly a dsDNA region, in close proximity to the masked promoter of which at least a portion of one strand of the double stranded region is complementary to the target nucleic acid, and a single stranded nucleic acid region, usually a ssDNA region, complementary to the target nucleic acid joined to the double stranded nucleic acid complementary strand. (Since, for the most part, the single and double stranded nucleic acid will be deoxyribonucleic acid, the stands will be referred to as DNA. The nucleic acid may be other than deoxyribonucleic acid, including ribonucleic acid, 2-lower alkyl ethers of ribonucleic acids (lower alkyl of from 1–3 carbon atoms), protein nucleic acids or other analog that allows for procession of RNA polymerases employed in the subject invention.)

The dsNA provides a clamp that locks the masked promoter into the inactive conformation of the probe. The template strand for transcription may be the strand complementary to the target nucleic acid, where the ssNA and dsNA complementary regions are joined, the strand having the same sequence as the target nucleic acid, or an arbitrary sequence. For the arbitrary sequence, the probe is designed to allow for either the target nucleic acid or a sequence complementary to the template arbitrary sequence to bind to the probe and initiate transcription. The inactive conformation is maintained in the absence of binding of the target nucleic acid, but upon binding of the target nucleic acid to the probe, the masked promoter is exposed for binding to an RNA polymerase, usually with prior binding to an initiator oligonucleotide that binds to the masked promoter to provide a "holopromoter." In effect, the dsNA of the same and complementary regions in relation to the target nucleic acid, act as a lock on the masked promoter with the target nucleic acid being the key that opens the lock.

In the presence of a template-dependent RNA polymerase and RTPs ("ribonucleotide triphosphates"), initiation and extension of RNA results, producing a ssRNA product. that is complementary to the template NA of the probe, usually a new copy of the target NA, usually target RNA. The complementary RNA or RNA homologous to the target RNA can repetitively bind to the probe to initiate the formation of additional copies of ssRNA, which can then repeat the process, so as to provide exponential amplification of the ssRNA copies.

The probe can be single stranded or double stranded, where only one strand comprises the masked promoter. The single stranded probe is characterized by having the masked promoter, usually primarily single-stranded DNA, joined at its 3' end with a sequence comprising a sequence at least substantially the same as a portion of the target NA sequence ("equivalent or same strand, for convenience, referred to as tss") and at its 5' end with a sequence complementary to the target sequence ("complementary strand, for convenience, referred to as the tcs") and having a dsNA portion proximal to the masked promoter and a ssNA portion distal from the masked promoter. The conformation of the probe results in steric constraints on the masked promoter, so as to diminish its ability to activate an RNA polymerase, which requires binding to the initiator sequence to form the holopromoter and the holopromoter binding to the RNA polymerase with initiation of formation of the complementary ssRNA. The double stranded probe, has one strand comprising at least a portion of the looped masked promoter joined at one end by the target identical or target complementary sequence and the other end by an arbitrary sequence. The second strand, which can be a single strand or comprise two strands, will be complementary to these two sequences, so that when the two strands are hybridized, at least a portion of the promoter region will be a single stranded loop. There will be a protruding or overhang region preferably at the 5' end of the template strand which will usually be complementary to the target nucleic acid. When an arbitrary sequence serves as the template strand, the template strand will have a protruding region joined to the remaining portion of the template, where the remaining portion will be hybridized to a complementary sequence. Where the second strand comprises two strands, each of the two strands will have two regions. A first region will be complementary to each other and the second region will be complementary to different portions of the first strand. The different portions will be on opposite sides of the promoter region. These various alternatives are depicted in FIG. 1 and will be further explained below.

In order to diminish the amount of initiation at the promoter in the absence of binding of the target sequence, various expedients are employed to reduce the ability of an initiator oligonucleotide to bind to the promoter region and the RNA polymerase to bind and process the transcription of the ribonucleic acid having the complementary sequence to the template. As will be described below, these include providing a bulky group adjacent the promoter region, which bulky group is displaced from the promoter region upon binding of the target sequence and providing for an inhibitory sequence to bind to the promoter region, which diminishes transcription initiation in the absence of binding of the target sequence.

By "holopromoter" is intended a promoter that is active in activating an RNA polymerase to initiate template dependent synthesis of an RNA strand. Of particular interest are RNA polymerases derived from bacteriophage, more particularly a T promoter, and particularly the T7 promoter, although other T promoters, such as T3 can also find use, as well as other bacteriophage promoters, such as SP6.

The T7 promoter has conserved residues from −17 to +6 relative to the start site of transcription, where the promoter may be considered to be divided into two domains, an initiation domain from −4 to +5 and a binding domain from −5 to −17. The initiation domain can be substantially eliminated, so that the nucleotides from −1 to −17 are all that are required. Single base changes in the binding domain of the T7 promoter reduce or eliminate promoter binding, but have little effect on the initiation of transcription. By way of contrast, single base changes in the initiation domain of the promoter have little effect on promoter binding but reduce the rate of initiation. The base pairs at −9, −10 and −11 appear to distinguish between T7 and T3, while the base pairs at −9 and −8 distinguish between T7 and SP6. In addition, nucleotides from the 5' and 3' ends may be removed while still retaining transcription initiation activity. Since any change tends to reduce the transcription rate, these modifications are generally not desirable.

The promoter region will be 17 bp, will usually have at least about 90% of the base pairs conserved, usually at least about 95% and more usually 100% conserved of the naturally occurring promoter region. In some instances, not more than 3, usually not more than 2, bases of the promoter region will be mismatched to the initiator oligonucleotide. For the most part, only the promoter region of −1 to −17 will be used and even in this region substantial variation is permitted while still retaining a substantial portion of the maximal activity. A portion of the promoter region may be double-stranded in the probe, usually not more than about 10 bp, usually not more than about 5 bp, and generally fewer than 3 bp. The portion of the promoter region that is double-stranded will generally be proximal to the 5' or 3' end of the promoter region.

For the most part, at least about 65% of the promoter region will be in a loop and single stranded. The loop may be a hairpin loop formed as a result of the probe being a single strand with the same strand and complementary strand being hybridized. See, for example, Cantor and Schimmel, Biophysical Chemistry, Part III, p. 1183, W. H.

Freeman & Co. (San Francisco 1980). Alternatively, it may be as a result of the probe being two strands, with the promoter region being present only in one strand, the "p strand" and the portions of the p strand proximal to the promoter being hybridized to the second or homologous strand of the probe.

To provide steric constraint to diminish the binding of the RNA polymerase to the promoter region as a single strand and/or to diminish the ability of the initiator strand to bind to the promoter region, the probe may take various conformations. These conformations are illustrated in FIG. 1, without intending to be exhaustive of the possibilities. The thick line in each of the figures is the target complementary sequence ("tcs"), that is the target sequence hybridizes to the sequence represented by the thick line. The thin line represents the sequence that is at least substantially the same as the target sequence ("tss"). The tcs serves as the template and will always have a portion that is double-stranded and a portion that is single-stranded. The tss will, for the most part, be double stranded and hybridized to the tcs.

In FIG. 1, FIG. 1A hybridization of the flanking sequences of the tcs and tss causes the promoter/initiator region to form a loop. Binding by the target RNA causes opening of the loop, with binding of the initiator to the promoter region and activation of the promoter with resulting binding of the RNA polymerase and initiation of RNA synthesis. Since a substantial amount of transcription can occur without binding of the target sequence to the probe, this embodiment will normally have a bulky group in the vicinity of the promoter region. FIG. 1B illustrates a similar masked promoter in which the tss also comprises a complementary sequence that is capable of hybridizing to a portion of the promoter/initiator region, so as to reduce the size of the loop. Provided that the portion of the promoter/initiator region that is hybridized is not more than about 5 bases, strand displacement by the target polynucleotide will sufficiently destabilize the loop to permit ring opening and activation of the promoter/initiator. FIG. 1C illustrates a masked promoter similar to that depicted in FIG. 1A, except that the tcs is bound to the promoter template at a site other than an end and the tss serves as the template sequence. This provides an alternative way to reduce the size of the loop. In effect, one strand is joined to a nucleotide between the ends of the promoter.

FIG. 1D illustrates a masked promoter varying from the one in FIG. 1A in that the 3'-end of the promoter/initiator region is bound to the tss at other than its 5'-end, so as to form a less flexible loop. FIG. 1E illustrates a masked promoter comprised of two separate strands, where the promoter/initiator region forms a loop by binding of its 3'-end to a tcs (narrow dark line) that comprises the tss. The tcs serves as the template sequence. In FIG. 1F the masked promoter differs from FIG. 1E except that the tss serves as the template sequence. FIG. 1G differs from that in FIG. 1F in that the promoter/initiator sequence-containing strand (thick dark line) is an arbitrary sequence unrelated to the target sequence. The tcs, which is on the other side of the promoter/initiator (thick shaded line) is at the 3'-end of the promoter/initiator region and hybridized to the tss (narrow shaded line) at the 5'-end of the complementary strand (narrow line). Strand displacement by the target sequence leads to opening of the loop, but the template sequence that codes for the RNA synthesis is unrelated to the target sequence. For detecting amplifying the arbitrary nucleic acid, a second probe must be used to which the target nucleic acid binds. This ancillary probe could be the same structure as in FIG. 1G, with the sequences reversed. That is, the arbitrary sequences indicated by broad and narrow dark lines would be the arbitrary related sequences and the other sequences indicated by the shaded lines would also be arbitrary sequence related. In this manner, the arbitrary sequence would be able to displace the second strand on either or both sides of the promoter region so that the initiator oligonucleotide could bind.

In FIG. 1H, a masked promoter is illustrated that is related to FIG. 1G, except that the promoter/initiator region complementary portions are on two strands that are hybridized to each other. The resulting duplex comprises tcs (thick shaded line) and tss (narrow shaded lines). The strand portions indicated by the two thick shaded lines may be capable of binding to the same target strand or to different target strands. Strand displacement by either of the target nucleic acid will cause opening of the loop and activation of the promoter/initiator region with copying of the template strand (thick dark line). In this embodiment, the strands will normally be related to the target nucleic acid. In FIG. 1J, the masked promoter differs from the masked promoter in FIG. 1F in that the 3'-end of a first strand is complementary to the 3'-end of the promoter/initiator region and the 5'-end of the first strand comprises a portion of the tss.

The probes may be used in solution or bound to a surface. Binding to a surface can be achieved by having the probes synthesized on a surface and the resulting array used for the analysis, or providing a terminal moiety that can bind to a reciprocal moiety on a surface, such as complementary oligonucleotides, ligand-receptor pairs, or employ a photo-activated compound that will react with the surface to form a covalent bond. Surfaces may include vessel walls, such as in microtiter wells, particles or beads, such as latex beads, Bioglas, polysaccharides, etc. The beads will generally be in the range of about 5 to 100μ. The probes may be retained on the solid surface during the reaction, so as to be retained upon isolation of the amplified nucleic acid.

With any of the masked promoters, transcription is activated by binding the initiator, a oligonucleotide DNA strand comprising a sequence complementary to the promoter/initiator sequence, which enables binding of an RNA polymerase to the resulting promoter/initiator complex. The initiator may be a single open strand or a double stranded stem having a small loop, usually fewer than about 8 bases, usually fewer than about 6 bases and may be from 1 to 2 bases. The double stranded portion will be at least about 2 bp, more usually at least about 3 bp, and not more than about 6 bp. When binding to the promoter, the initiator will open the double stranded part to bind to the promoter. When the promoter is masked, in its sterically inhibited conformation, transcription is inhibited, by the failure to form the holo-promoter and/or allow for procession of the RNA polymerase along the template strand. Upon strand displacement by the target nucleic acid or a nucleic acid acting in an equivalent manner, the promoter region is no longer constrained in the loop, nor is progression of the RNA polymerase inhibited and binding by the initiator initiates transcription, where the RNA polymerase may progress along the template stand and produce a complementary copy of the template strand.

Because of the amplification resulting from the use of the subject probes, the amount of transcription independent of the target nucleic acid should be minimal. Therefore, other constraints will usually be employed to substantially prevent background transcription. One such constraint is the presence of a blocking group bound to the strand complementary to the template strand, which effectively sterically inhibits the progression of the RNA polymerase. This can be imagined with the embodiments described above, where for example, in FIG. 1A a large bulky group would be joined to a nucleotide of the tss (narrow dark line) adjacent the promoter region (hatched line). The bulky blocking group adjacent to the promoter/initiator region, serves not only to prevent progression of the RNA polymerase, but also serves to inhibit binding of the initiator and the RNA polymerase to the promoter region.

Various techniques can be used to provide a sterically inhibiting molecule. Steric inhibition will normally be employed where the initiation of transcription in the absence of the target sequence is greater than about 10%, usually when greater than about 5%, and even when greater than about 1%. Usually, the molecule will be at least about 1 kDal, more usually, at least about 5kDal and may be 50 kDal or more. Conveniently, a small molecule modified nucleotide may be used, namely a molecule of less than about 1 kDal, which can serve as a ligand to a large molecule. One or more modified nucleotides may be used in the synthesis of the strand complementary to the template strand (For simplicity, this will be referred to as the tss, which will normally be such strand, and can be used as exemplary of the arbitrary strand complementary to the template strand.) where the modified nucleotide(s) will be within 10 bases, usually within 5 bases and preferably within 2 bases of single stranded portion of the promoter/initiator. Therefore, the modified nucleotide may be a nucleotide complementary to a nucleotide present in the promoter/initiator region, proximal to the 5' end of the region, or in the region adjacent to the promoter region, particularly having the same sequence as the target sequence.

Various ligands may be used that have a naturally occurring or synthetic receptor. The receptor may be monovalent, having only one binding site for the ligand, or polyvalent, having more than one site for binding the ligand. Naturally occurring ligand-receptor pairs include biotin-strept/avidin, substrates-enzymes, steroids-steroid receptors, hormones-surface membrane receptors, etc. For compounds that do not have naturally occurring receptors, one may prepare antibodies to haptens, where the antibodies may be antisera or monoclonal antibodies. Ligands with their complementary antibodies include digoxin-antidigoxin, fluorescein-antifluorescein, dinitrobenzene-antidinitrobenezene, rhodamine-antirhodamine, etc. Where the receptor is polyvalent, it may be made monovalent, such as Fab fragments of antibodies, monovalent fragments of strept/avidin, etc. Modified nucleotides are well known and commercially available and may be used in lieu of the naturally occurring nucleotide during synthesis of the probe. In some instances, there may be advantages to have a fluorescer hapten, where the fluorescer is quenched by the antifluorescer, so that one could titrate when at least substantially all of the fluorescer is bound to antifluorescer.

While it will usually be more convenient to use a small molecule modified nucleotide, one may directly bind large molecules to provide the modified nucleotide. Thus, bulky groups may be synthetic polymers, proteins, dendrimers, polysaccharides, particles, such as Bioglas, latex, Agarose, etc. To provide further constraint, these bulky groups may be bound to the receptors to further enhance the steric inhibition at the promoter region.

Inhibition of transcription initiation in the absence of binding of the target nucleic acid can be further enhanced using a short nucleic acid strand as an exogenous inhibitor that can bind to a portion of the promoter region, particularly in the promoter region of −17 to −6. The inhibitor sequence would be comprised of bases that inhibit binding of the RNA polymerase, such as ribonucleotides, protein nucleotides, modified nucleotides (such as bulky groups), etc., where upon binding of the target nucleic acid to the probe, the initiator could bind and displace the inhibitor. Alternatively, the tss strand may be separated from the promoter region by an arbitrary sequence of from about 2 to 30, usually about 5 to 20 nucleotides. An exogenous inhibitor would bind to this short separating arbitrary nucleic acid strand, as well as into the promoter region. Particularly, the exogenous inhibitor could bind to the initiation region, including one or more mismatches and even extend into the promoter region −6 to −17 by having mismatches at conserved nucleotides, where the mismatches interfere with binding of the RNA polymerase. Modified nucleotides could be used, such as protein nucleic acids (amino acid backbone) or nucleotides with side chains to interfere with the binding of the RNA polymerase. The exogenous inhibitor would be displaced by the initiator when the target nucleic acid displaces the tss, since the initiator would have a higher affinity for the promoter region than the exogenous inhibitor, particularly where the tss is no longer bound to the tcs.

Joined to the masked promoter will be two nucleic acid moieties. With a single stranded probe, joined to the 5' end of the promoter region will be the tcs (template sequence), while bound to the 3' end of the promoter region will be the tss. The tss will be shorter than the tcs sequence, so as to leave a protruding region or overhang to which the target sequence initially binds and then displaces the tss.

Where there are two strands, the tcs sequence will be bound to the 3'-end of the promoter region, but the tss will be on the other strand hybridized to the tcs. Again, the tcs will be longer than the tss and will provide a protruding sequence for binding the target sequence. In addition, greater flexibility is achieved with having two strands substituting for the single strand that binds to the p/i strand, as described for FIG. 1H. The numerous variations have already been discussed in relation to FIG. 1, which are not intended to be exclusive , but rather illustrative.

The tcs or template strand may have a terminal sequence other than a sequence complementary to the target nucleic acid. This sequence may play a variety or roles. In one role it may be used to hybridize to a complementary sequence bound to a surface to permit the probes to be bound to the surface prior to, during or after the amplification. The terminal sequence may serve for isolation of the amplified nucleic acid by combining the reaction mixture with beads, surface, capillary or packed column to which the complementary sequence is bound. The terminal sequence may be used for visualizing the amplified nucleic acid by having a complementary sequence with a detectable label bind to the terminal sequence. The labeled amplified nucleic acid could then be analyzed by chromatography or electrophoresis to enrich for particular nucleic acids. Therefore, the terminal sequence can be used as a vehicle for linking a complementary sequence, which may be modified in any way of interest, e.g. detectable label, for further analysis. If stronger bonding of the complementary sequence is desired, intercalators may be used, particularly those that fluoresce, or photoactivated molecules that will covalently link the complementary sequence to the terminal sequence.

The hybridized tcs and tss form a clamp to constrain the promoter region in a particular conformation as a single strand, inhibited from binding to the initiator. The clamp or double stranded portion will have at least about 6 bp, usually at least about 10 bp, more usually at least about 12 bp and not more than about 60 bp, usually not more than about 30 bp. The number of base pairs will depend on the melting temperature of the clamp, the temperature at which the amplification is carried out and the rate at which the clamp is unzipped by the invading target sequence. The protruding portion of the strand will have at least about 6 bases, usually at least about 10 bases, more usually at least about 12 bases, usually not more than about 30 bases, more usually not more than about 20 bases.

The total number of bases of the probe, whether single or double stranded, will be at least about 50, usually at least about 50 and not more than about 160, usually not more than about 120 bases. For the single stranded probe, usually the strand will be at least about 50 and usually not more than about 120, while for the double stranded probe, each strand will usually be at least about 40 and not more than about 120, usually at least about 45 and not more than about 100.

The initiator will be DNA complementary to at least substantially all of the promoter region which has 17 bases, although small truncations of up to 6 bases are permissible, particularly in the initiation region. Desirably, the full sequence will be used. While the RNA polymerase will recognize a DNA/RNA hybrid, the hybrid is less efficient in initiation and would normally not be used.

The sample that serves as the source of the nucleic acid to be amplified and analyzed may come from viral nucleic acid, prokaryotic or eukaryotic nucleic acid, bacteria, protista, invertebrates, vertebrates, particularly mammals, etc. The subject methodology is particularly applicable to complex mixtures having large numbers of different nucleic acids, where the target nucleic acid may be a single target or a plurality of targets, both DNA and RNA, particularly mRNA. The sample will provide at least about 1 attomole of each of the target nucleic acids, usually at least 1 femtomole and preferably at least one picomole. Obviously, much larger amounts of target nucleic acid may be used and the amount of each target nucleic acid may vary over a range of about 1 to $10^{-5}$, usually from about 1 to $10^{-4}$.

Depending on the source of the sample, the sample may be subjected to various prior processing before being used in the transcriptional amplification. The source may be individual cells of the same type or mixed type, as in tissue, biopsy, swab, blood, lymph fluid, CNS fluid, urine, saliva, waste water, soil, effluents, drinking water, cooling water, foods, agricultural products, drugs, etc., may be a single culture, cell line, primary cells, or the like. The cells may have been subject to prior separation by means of FACS, immunoseparation using antibodies that bind to specific markers, or other selection means. Depending on the nature of the sample, the sample may be subject to concentration, precipitation, filtration, particularly microfiltration, chromatography, etc. For cells, the cells will be lysed by any convenient means, using detergents, mechanical disruption, e.g. sonic disruption, etc. Where RNA is the target, RNase inhibitors, such as PMSF may be added, the sample heated, or the like, to prevent degradation of the RNA. Nucleic acid precipitation may be employed to isolate the DNA, which may then be degraded using restriction enzymes, mechanical disruption, etc. Nucleic acid preparation can follow well recognized techniques, such as those described in "Molecular Cloning: A Laboratory Manual" (Cold Springs Harbor Laboratory Press, Cold Spring Harbor, N.Y., 1989), Mach et al., The Annual of Biological Chemistry (1986) 261:11697–11703; Jeffries et al., J. of Biol. Chem. (1994) 269:4367–4372; and U.S. Pat. Nos. 5,654,179 and 5,993,634.

The reaction mixture is prepared by combining the sample, which will usually have been previously processed, the probe, RTPs, RNA polymerase, initiator and as appropriate other agents, such as receptors, exogenous inhibitors, and the like. A suitable buffered medium is employed for performing the transcription. Temperatures will vary in the range of about 10 to 50° C. The temperature will be maintained substantially constant. While the temperature may be cycled, it is unnecessary and usually undesirable. The concentration as to each of the target nucleic acids will generally be at least about 0.02 aM (1 copy/100 ul), usually at least about 0.2 aM and will usually not exceed about 0.2nM ($10^{10}$ copies/100 ul). The concentration of each probe for each target nucleic acid will be in the range of about 0.2 pM to 0.2 uM, more usually in the range of about 0.2 pM to 0.2 nM. The concentration of initiator will be based on the total concentration of probes and will generally be about n –100 n:1, where n is the level of multiplexity of the assay, depending on the likelihood of finding all of the target nucleic acids present in a sample, the total number of different probes, the sensitivity of the system to initiation in the absence of target nucleic acid, and the like. The NTPs will generally be present for each NTP at a concentration in the range of about 0.1 mM to 10 mM to be able to produce RNA products of up to 1000 times probe concentration. The RNA polymerase will generally be present at a concentration in the range of about 0.1 IU to 100 IU. The receptors will be present on a 1:1 basis to the ligand and may be in excess in the medium, usually not more than about 2-fold excess. The exogenous inhibitor may be present in the range of about 0.5–10 fold based on the total probes, usually about 2–5 fold.

While the subject system can be used for the multiplexed determination of a plurality of nucleic acid targets, two or more, only one probe may be used or more than one, usually not more than about 50 probes, more usually not more than about 20 probes. The number of probes will depend to some degree on the differences in the target nucleic acids as to sequence and amount, whether the analysis is quantitative, semiquantitative or qualitative, whether low abundance nucleic acid targets can be enriched, etc.

Desirably, a control is employed, which may be one or more known nucleic acids that are added in known amount with the complementary probe. The concentration of the nucleic acid that is added will generally be equal to or greater than the anticipated concentration of the lowest concentration target nucleic acid, generally not more than 100-fold greater, usually not more than about 10-fold greater. The amount of the amplified nucleic acid can then be used to normalize the target nucleic acids. By using two different concentrations of control nucleic acids, one can see the effect of concentration on the amount of amplified nucleic acid produced and adjust the observed amounts accordingly.

The medium which is employed will be conventional and includes such media as 30 mM $MgCl_2$, 40 mM Tris-HCl, 1 mM Spermidine, 0.01% Triton X-100, DTT, 80 mg/ml Polyethylene Glycol, 4 mM ATP, 4 mM GTP, 4 mM CTP, 4 mM UTP, pH 8.0.

The reaction will be carried out for sufficient time for a sufficient amount of the least prevalent target nucleic acid to be amplified to a detectable amount. Generally the reaction will be incubated for at least about 10 min, usually at least about 20 min and not more than about 12 h, more usually not more than about 6 h. Desirably for each target nucleic acid, as least about 1pmole of nucleic acid will be produced, more desirably at least about 100 pmoles, particularly 1 nmole.

The amplified nucleic acid may be analyzed in a number of different ways. One may use individual insoluble complementary sequences or arrays to bind the amplified sequences at particular sites and a second labeled sequence complementary to a region of the nucleic acid copies not involved in binding to the surface to bind to the sequestered nucleic acids. The label at a particular site associated with a particular sequence will then indicate the presence of the target nucleic acid as well as the amount, where the complementary sequence bound to the surface is in excess as compared to the amplified nucleic acid. Alternatively, one may use labeled RTPs, e.g. fluorescently labeled uridine, so that the amplified nucleic acids are fluorescent. Upon binding to the surface at a particular site, the amplified nucleic acid would be detected. Where the amplified target nucleic acids have different molecular weights, using labeled RTPs, they can be separated by electrophoresis and characterized by their migration rate.

By being able to measure semi-quantitatively or quantitatively the level of transcription in a cell or lysate, the subject method finds applicability in evaluating the effect of changes in the cellular environment on gene usage. Not only can one determine the genes that are being transcribed, but differences in splicing can also be detected. In this way, aberrant cells may be compared to normal cells, such as neoplastic cells, inflamed cells, genetically modified cells, cells comprising mutations, etc. One can also measure changes in transcription as cells mature, differentiate, dedifferentiate, transform from one cell type to another, e.g. fibroblast to myoblast, etc. The changes in environment may include such changes as candidate drugs, feeder layers, changes in media, changes in factors, etc. In this way one can analyze the physiology of a cell and its response to various changes. Also, the knowledge of the transcriptional level of one or more mRNAs gives an indication of the level of protein present in the cell. One can obtain as a first iteration, the effect of changes in the environment of the cellular response at the mRNA level and by extrapolation, at the protein level.

Kits can be provided having one or more probes, up to 100 or more probes, where the kits can conveniently provide the other reagents, such as RNA polymerase, RTPs, as well as modified RTPs, ancillary reagents, such as receptors for ligands, exogenous inhibitors, initiators, media and the like. The probes may be in solution, as a dispersible powder or bound to a surface, being present in a microtiter well of a microtiter plate, bound to beads, or the like. The microtiter plate allows for 96 or 384 or more assays to be performed substantially simultaneously under comparable conditions.

The following examples are offered by way of illustration and not by way of limitation.

EXPERIMENTAL

Materials

Two DNA probes, one DNA promoter, and one RNA target are synthesized and purified.

P1 (probe)
  5' TCCTTCCTTCTCTGTTGCCACTTCAGC-CtatagtgagtcgtattaGGCTGAAGTGGCAA Note: the underlined C is biotinylated, and lower case letters represent promoting region complementary to promoter P17.

P1c (probe)
  5' TCCTTCCTTCTCTGTTGCCACTTCAGC-CtatagtgagtcgtattaAAAAAAAAAAAAA Note: the underlined A is biotinylated, and lower case letters represent promoting region complementary to promoter P17.

P17 (promoter)
  5' TAATACGACTCACTATA

R1 (RNA target)
  5' CACAGAGGCUGAAGUGGCAACAGAGAAG-GAAGGAGAAGA

P1 is the probe, which can fold into a hairpin structure with a 13 base loop:

P1C is the control probe which cannot fold to any stable structure and is linear all the time:

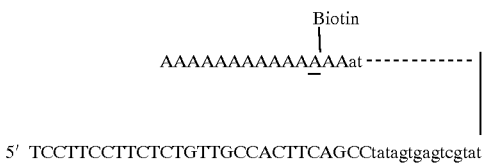

RNA target R1 can hybridize to both P1 and P1C to form the following duplexes:
  P1-R1 duplex:

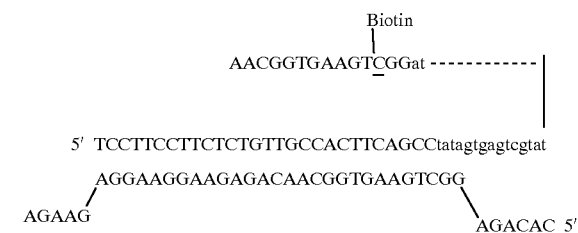

P1C-R1 duplex:

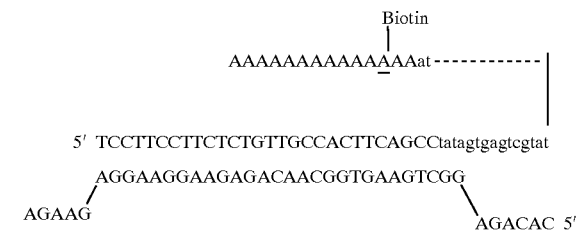

Streptavidin is purchased from Boehringer Mannheim. T7-MEGAshortscript T7 transcription kit is purchased from Ambion Corporation, Austin, Tex.

Transcription reactions

For each reaction (in duplicate), mix 2 ul of 200 nM probe (P1 or P1C), 2 ul of 200 nM of P17, 2 ul of 2 uM streptavidin, and 2 ul of RNA targets R1 with the following different concentrations: 0, 0.002, 0.02, 0.2, 2, 20, and 200 nM. To the mixture, add 2 ul of 10× transcription buffer, 2 ul of 75 mM ATP, 2 ul of 75 mM GTP, 2 ul of 75 mM CTP, 2 ul of 75 mM UTP, and 2 ul of T7 MEGAshortscript Enzyme Mix. Total volume is 20 ul. Incubate at 37C on ABI 4800 and stop the reactions after 0.25, 0.5, 1, 2, 4, and 8 hour by adding 2 IU DNase I and incubating for another 15 mins. Then to each tube, add denaturing gel loading buffer, heat to 95C for 3 mins, and snap cool on ice. Load 10 ul of the above mixture to 15 TBE-UREA gel (Invitrogene Inc., Carlsbad, Calif.). 1× TBE running buffer contains 0.089 M Tris-HCl, 0.089 M Boric Acid, 2 mM EDTA, pH8. Gel is run at 200 volts for 1 hour, stained with SYBR Gold fluorescence staining solution (Molecular Probes Inc, Eugene, Oreg.). RNA products are visualized and quantified using Epi Chemi II Darkroom gel imaging system (UVP, Inc. Upland, Calif.).

Results

With P1C probe, 28-nucleotide RNA product yield is high, regardless of RNA target concentration, as expected. With P1 probe and no RNA targets, there is no RNA product detected even after 8 hours of reaction. With P1 probe and RNA targets, RNA yield increases with the amount of RNA target input, as well as time of reaction. Plot of RNA yield vs time indicates there is a dose response and exponential amplification. RNA yield threshold is set and the threshold time TT is defined as the time when RNA yield is at the threshold level. Plot of TT vs input RNA concentration gives smooth standard curve, indicating a good dose response, with 5 logs of dynamic range and <2 pM detection limit. Sensitivity will be much improved downscaling concentration of probes and targets, by using more sensitive detection methods, such as radioactivity and northern blotting.

This experiment demonstrates the isothermal and exponential amplification characteristics of the invention.

The subject method allows for detection of mRNAs, particularly low abundance mRNAs in a complex mixture, particularly a cellular mixture, such as a lysate. The cellular mixture does not require substantial processing to be able to detect low-level mRNAs, so as to obtain a better profile of the transcriptional level of a cell. The method can be used in drug screening, in diagnosis, evaluation of the effect of drugs or combinations of drugs during treatment of diseases, identification of cell type, and studying the effect of changes in the environment related to changes in the transcriptional profile of cells. By combining the subject methodology with other assay techniques, such as proteomics, one can obtain a detailed insight into the events occurring in cells in response to screening of drug candidates, treatment of diseases, etc.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. While the invention has been described in detail with reference to certain preferred embodiments thereof, it will be understood that modifications and variations are within the spirit and scope of that which is described and claimed.

What is claimed is:

1. A method for determining at least one target nucleic acid in a complex mixture of nucleic acids, employing a probe for each of said target nucleic acids, where said probe is characterized by having a masked RNA polymerase promoter as a single-stranded loop inhibited from initiating transcription, a template sequence 5' of said masked promoter complementary to said target nucleic acid and comprising a double stranded nucleic acid region portion acting to inhibit transcription, with the proviso that when said transcription is greater than about 10% of the transcription in the presence of said target sequence, a bulky group is bound to said double stranded nucleic acid region, whereby when a sequence complementary to said template binds to said template sequence, said inhibition is released, said method comprising:

combining and incubating said sample, probe, an initiator comprising a sequence complementary to said, RNA polymerase and RTPs under transcriptional conditions, whereby target nucleic acid binds to said template sequence enabling transcription to produce a transcript complementary to said template, wherein said transcript further binds to said template releasing inhibition of transcription, so that the process is repeated amplifying said transcript, and analyzing said complementary nucleotide as an indication of the presence of said target nucleic acid.

2. A method according to claim 1, wherein said double stranded nucleic acid is dsDNA and a bulky group is present proximal to said masked promoter and bonded to the strand in the dsDNA region complementary to said template strand.

3. A method according to claim 1, wherein said template sequence comprises an arbitrary terminal region joined to said template sequence; and comprising the additional step for said analyzing of;

binding said terminal region complementary sequence of said transcript to a terminal region sequence bound to a support or a detectable label.

4. A method according to claim 1, wherein said RNA polymerase is the T7 polymerase and said masked promoter is the T7 promoter.

5. A method according to claim 1, wherein the source of said sample is a cellular lysate.

6. A method according to claim 1, wherein said initiator is a stem and loop, one strand and said loop comprising a sequence complementary to said promoter sequence.

7. A method for determining at least one target nucleic acid in a complex mixture of nucleic acids, employing a probe for each said target nucleic acids where said probe is characterized by having a masked RNA polymerase promoter inhibited from initiating transcription by an RNA polymerase, a strand bound to the 3'-end of said promoter comprising a sequence at least substantially the same as the target nucleic acid for said probe ("tss") and a template complementary strand bound to the 5'-end of said promoter and protruding beyond said tss ("tcs"), wherein the binding of said tss and tcs results in the masking of said promoter, with the proviso that when said transcription initiation is greater than about 10% of the transcription initiation in the absence of said target sequence, a bulky group is bound to said tss sequence proximal to said initiation region, said method comprising:

combining said complex mixture with said at least one probe for each target nucleic acid, RNA polymerase, a transcription initiator comprising a complementary sequence to said promoter and RTPs under conditions of template-dependent transcription;

incubating said mixture for target nucleic acid to bind to said tcs and release said tss from said tcs with the unmasking of said promoter and the binding of said transcription initiator to said single stranded promoter, whereby repetitive template-dependent transcription occurs to produce transcripts; and determining the presence of said transcripts.

8. A method according to claim 7, wherein a bulky group is bound to said tss strand proximal to said masked promoter.

9. A method according to claim 7, wherein said template sequence comprises an arbitrary terminal region joined to said template sequence; and comprising the additional step for said determining of;

binding said terminal region complementary sequence of said transcript to a terminal region sequence bound to a support or a detectable label.

10. A method according to claim 7, wherein said RNA polymerase is the T7 polymerase and said masked promoter is the T7 promoter.

11. A method according to claim 7, wherein the source of said sample is a cellular lysate.

12. A method according to claim 7, wherein said probe is a hairpin comprising a stem and loop with said masked promoter in said loop.

13. A method according to claim 7, wherein said probe comprises two strands, a first masked promoter strand and a second complementary strand comprising a sequence complementary to a portion of said masked promoter strand to form a dsDNA region, said portion proximal to said masked promoter, whereby said masked promoter is a single stranded loop.

14. A method according to claim 13, wherein said second strand has a region complementary to a portion of said masked promoter strand distal from said dsDNA region.

15. A method according to claim 13, wherein said second strand comprises two strands, each binding to said masked promoter strand on opposite sides of said promoter.

16. A kit comprising a plurality of probes characterized by having a single stranded masked RNA polymerase promoter unable to initiate transcription, a template sequence 5' of said masked promoter, a sequence complementary to said target nucleic acid and a dsNA region proximal to said masked promoter and acting to inhibit initiation of transcription, whereby when target nucleic acid binds to said probe, said initiation inhibition is released and said transcription is initiated, with the proviso that when said transcription initiation is greater than about 10% of the transcription initiation in the absence of said target sequence, a bulky group is bound to said complementary sequence proximal to said initiation region, and an initiator having a complementary sequence to said masked promoter.

17. A kit according to claim 16, wherein said dsDNA region comprises a bulky group or a hapten capable of binding to a bulky group bound to the strand complementary to said template sequence and proximal to said masked promoter.

18. A kit according to claim 16, wherein said probe is a single strand comprising a stem and loop and said masked promoter is in said loop.

19. A kit according to claim 16, wherein said probe comprises two strands having complementary sequences with one strand comprising said masked promoter and the binding of said strands results in said masked promoter being in a single stranded loop.

20. A kit according to claim 16, wherein said initiator has a stem and loop conformation.

* * * * *